United States Patent
Zhang et al.

(10) Patent No.: US 7,230,245 B2
(45) Date of Patent: Jun. 12, 2007

(54) FIELD INDUCED THZ WAVE EMISSION MICROSCOPE

(75) Inventors: Xi-Cheng Zhang, Melrose, NY (US); Tao Yuan, Troy, NY (US); Jingzhou Xu, Troy, NY (US); Haewook Han, Pohang (KR)

(73) Assignee: Rensselaer Polytechnic Institute, Troy, NY (US)

( * ) Notice: Subject to any disclaimer, the term of this patent is extended or adjusted under 35 U.S.C. 154(b) by 193 days.

(21) Appl. No.: 11/121,385

(22) Filed: May 4, 2005

(65) Prior Publication Data

US 2006/0022141 A1 Feb. 2, 2006

Related U.S. Application Data

(60) Provisional application No. 60/567,990, filed on May 4, 2004.

(51) Int. Cl.
*G01J 5/02* (2006.01)
(52) U.S. Cl. .................................. 250/341.1
(58) Field of Classification Search .............. 250/341.1
See application file for complete search history.

(56) References Cited

U.S. PATENT DOCUMENTS 5,894,125 A * 4/1999 Brener et al. ............... 250/330

| 6,734,974 | B2 | 5/2004 | Jiang et al. |
| 6,762,397 | B2* | 7/2004 | Takami et al. ........... 250/201.3 |
| 6,828,558 | B1* | 12/2004 | Arnone et al. ........... 250/341.1 |
| 2006/0022141 | A1* | 2/2006 | Zhang et al. ............ 250/341.1 |
| 2006/0151722 | A1* | 7/2006 | Cole et al. ............... 250/493.1 |

OTHER PUBLICATIONS

Q. Wu and X.-C. Zhang, Free-Space electro-optic sampling of terahertz beams, Applied Physics Letters, Dec. 11, 1995, pp. 3523-3525, vol. 67, No. 24.
Hou-Tong Chen and Roland Kersting, Terahertz imaging with nanometer resolution, Applied Physics Letters, Oct. 13, 2003, pp. 3009-3011, vol. 83, No. 15.

* cited by examiner

*Primary Examiner*—Albert J. Gagliardi
*Assistant Examiner*—Christopher Webb
(74) *Attorney, Agent, or Firm*—RatnerPrestia

(57) ABSTRACT

A device for use with a source of radiation to provide a THz emission image representing a sample. The device comprises a substrate, a metallic probe having a tip adjacent to the substrate surface and a source of AC bias coupled between the probe tip and substrate. Radiation generated by the source of radiation is incident on the substrate surface in the vicinity of the probe tip and generates THz emission based at least on the AC bias coupled between the probe tip and substrate. A method for providing a THz emission image representing a sample is also provided.

25 Claims, 12 Drawing Sheets

FIELD INDUCED THZ WAVE EMISSION MICROSCOPE

CROSS REFERENCE TO RELATED APPLICATIONS

This application claims priority of U.S. Provisional Application Ser. No. 60/567,990, filed on May 4, 2004, the contents of which are incorporated herein by reference.

STATEMENT REGARDING FEDERALLY SPONSORED RESEARCH

The present invention was developed under National Science Foundation Grants ECS-0140459 and ECS-0245461. The U.S. government may have certain rights to the present invention.

TECHNICAL FIELD

The present invention relates generally to microscopes and microscopy and, more specifically, to sub-wavelength emission imaging in the terahertz (THz) frequency range.

BACKGROUND OF THE INVENTION

THz radiation occupies a large portion of the electromagnetic spectrum between the infrared and microwave bands, namely the frequency interval from 0.1 to 10 THz, and is a developing frontier in imaging science and technology. In contrast to the relatively well-developed techniques for imaging at microwave and optical frequencies, however, there has been only limited basic research, new initiatives and advanced technology developments in the THz band.

THz time-domain spectroscopy (THz TDS) allows exploration of the rich spectroscopic information on molecular vibrations, rotations, and other low-energy transitions in biological and organic compounds, and semiconductor structures. Biological and organic compounds have distinct signatures within the THz region of the electromagnetic spectrum, such as molecular vibrational and rotational levels, and their chemical compositions can be examined with THz wave microscopic systems.

Unlike X-rays, THz radiation has low-photon energy (4 meV @ 1 THz), low average power (nW to μW) and does not subject biological tissue to harmful radiation. THz radiation can be focused to give sharper images. In addition, THz radiation provides spectroscopic information about the chemical composition, as well as the shape and location of the samples it is imaging.

Unlike common optical spectroscopes, which only measure the intensity of light at specific frequencies, THz time-domain spectroscopic techniques directly measure the THz wave's temporal electric field. Fourier transformation of this time-domain data gives the amplitude and phase of the THz wave pulse, therefore providing the real and imaginary parts of the dielectric constant without the use of Kramers-Kronig relations. This allows precise measurements of the refractive index and absorption coefficient of samples that interact with the THz waves.

SUMMARY OF THE INVENTION

The present invention is embodied in a device for use with a source of radiation to provide a THz emission image representing a sample. The device comprises a substrate, a metallic based probe disposed adjacent a first surface of the substrate, the probe having a tip portion at one end thereof, and a source of AC bias coupled between the metallic based probe tip and a further surface of the substrate. Radiation generated by the source of radiation is incident upon the first surface of the substrate in a vicinity of the metallic based probe tip and a THz radiation is emitted from the first surface of the substrate based at least on the AC bias.

The present invention is also embodied in a method for providing a THz emission image representing a sample for use with a source of radiation. The method includes providing a substrate and disposing a metallic based probe adjacent a first surface of the substrate, the metallic based probe having a tip portion at one end thereof. The method further includes coupling a source of AC bias between the metallic based probe and a further surface of the substrate. The method further includes emitting the radiation from the source of radiation toward the first surface of the substrate in a vicinity of the tip portion of the metallic based probe and emitting a THz radiation from the first surface of the substrate responsive to at least the AC bias based on the radiation emitted from the source or radiation.

The present invention is further embodied in a microscope for use with a source of radiation for producing a THz emission representing an image of a sample. The microscope comprises a substrate and a metallic based probe disposed adjacent a first surface of the substrate, the probe having a tip portion at one end thereof. The microscope further includes a source of AC bias coupled between the metallic based probe tip and a further surface of the substrate. The microscope further includes an actuator coupled to the metallic based probe, the actuator changing an X and/or Y axis position of the metallic based probe relative to a plane parallel to the first surface of the substrate. The microscope further comprises a THz detector for modulating the source of radiation with a sample-modified THz radiation to create a modulated THz radiation characteristic of the sample and an optical detection system for modifying and detecting the modulated THz radiation and converting the modulated THz radiation into electronic information. The microscope further comprises a processor for receiving the electronic information and producing an image of the sample based on the electronic information and the position provided from the actuator. The sample is placed on the substrate, and radiation generated by the source of radiation is incident upon the first surface of the substrate in a vicinity of the metallic based probe tip and sample, and the sample-modified THz radiation is emitted from the first surface of the substrate based at least on the AC bias.

These and other aspects will become apparent in view of the accompanying description.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Due to the diffraction-limit, the standard imaging resolution for 1 THz has historically not been much smaller than 300 μm. Near-field imaging techniques are known that can greatly improve the spatial resolution of a THz wave sensing and imaging system.

Aperture and dynamic aperture techniques applied to THz microscopy are known in the art. These techniques are all passive imaging in the sense that an incident THz radiation is required in their techniques to generate THz radiation. For the sub-wavelength resolution needed for THz imaging, a sub-wavelength structure is typically employed to limit the beam size. Conventional methods use a small aperture. When a sub-wavelength sized aperture is used, however, the transmitted beam has a very small throughput. An apertureless method may use a metal probe to enhance the spatial resolution, thus it may increase throughput.

An apertureless THz near-field emission microscope performs active imaging according to an exemplary embodiment of the present invention. The microscope desirably provides active imaging in that a THz signal is emitted from a semiconductor wafer surface by optical pumping, but without requiring an incident THz wave. The exemplary microscope is apertureless in that a tapered metal probe with a nearly circular aperture is placed near a surface of the semiconductor wafer, rather than requiring a dynamic or physical aperture. In an exemplary embodiment of the THz near-field emission microscope, the tapered metal probe is coupled to the substrate with a source of AC bias. An optical pump beam incident on the AC biased apertureless semiconductor wafer induces dipole moments below the wafer surface and generates a photocurrent that emits a THz pulse.

Figure 1:
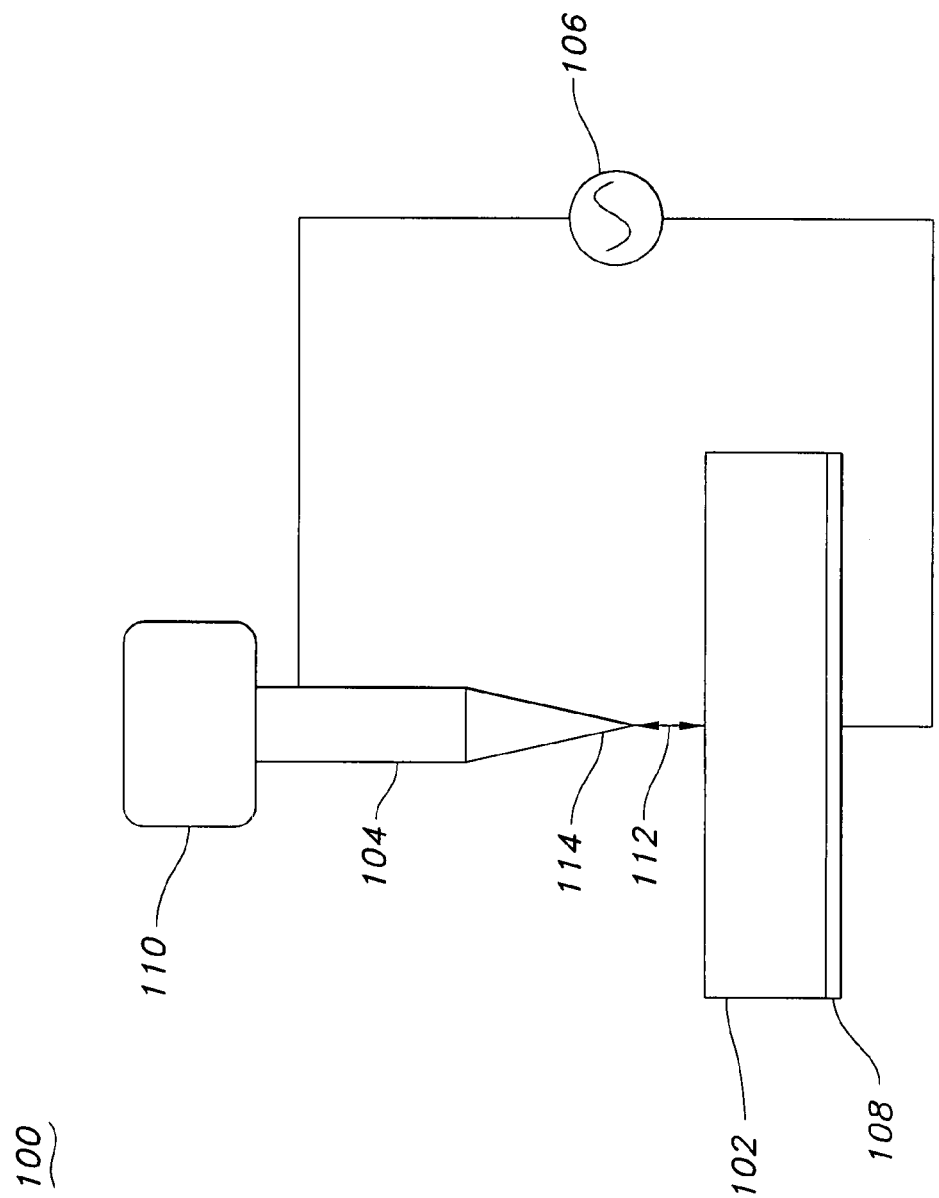
FIG. 1 is a side view illustration of an exemplary apertureless THz emission microscope of the present invention.

Referring now to FIG. 1, a first embodiment of an apertureless THz emission microscope 100 is illustrated. As shown in FIG. 1, a substrate 102 may desirably be coupled to a tapered metal probe 104 via a source of AC bias 106. A contact 108 for accepting an electrical connection may be placed on a surface of the substrate 102. An actuator 110 may be coupled to the tapered metal probe to provide a variable distance 112 between the metal probe 104 and the substrate 102.

Although contact 108 is shown on a bottom surface of the substrate 102, the invention is not so limited in that the contact may be on another surface of the substrate. Contact 108 may be a contact pad and, although contact 108 is shown as spanning the bottom surface of substrate 102, the contact may be connected to a portion of any surface of the substrate designed for accepting an electrical contact.

Substrate 102 may desirably be a semiconductor wafer. The semiconductor wafer may be n-type or p-type doped with various dopant concentrations. According to one exemplary embodiment, the substrate may be InAs or GaAs, each of n-type or p-type doping. The invention is not limited to these materials however, and any semiconductor material, for example Si, may be used. Substrate 102 may be a single layer or multiple layers of materials, such as multiple layers of n-type or alternating n-type and p-type doping. It is contemplated that substrate 102 may be formed of any structure provided that a surface of substrate 102 be conductive.

In one exemplary embodiment, tapered metal probe 104 may be formed from Tungsten or Pt—Ir. Other metallic compositions may be used without limiting the scope of the invention. Tapered metal probe 104 has a tip portion 114 which may desirably have a diameter between about 1 nm to 1 μm adjacent to substrate 102, although other diameters may be used without limiting the scope of the invention. According to the present invention, a smaller diameter of the tip portion desirably provides a finer spatial resolution. Thus, the diameter of tip portion 114 may provide spatial resolution variability.

Actuator 110 desirably provides a variable distance 112 between tapered metal probe 104 and substrate 102. Although not shown in FIG. 1, the actuator may also desirably provide lateral positioning of the tapered metal probe 104 across the surface of the substrate 102. In one exemplary embodiment, the actuator is a piezo actuator capable of providing 0.1 nm resolution in at least the vertical and/or lateral directions.

Source of AC bias 106, is desirably coupled between substrate 102 and tapered metal probe 104. The source of AC bias 106 provides dipole moments below the surface of the substrate. In one exemplary embodiment, the AC bias voltage is between 0 to 5 V rms. Although an exemplary voltage range is provided, it is contemplated that other bias voltages may be used within the scope of the invention. It is contemplated that any frequency of AC bias may be selected. The frequency of AC bias is desirably selected to provide a minimal noise input into a THz image measurement.

Figure 2:
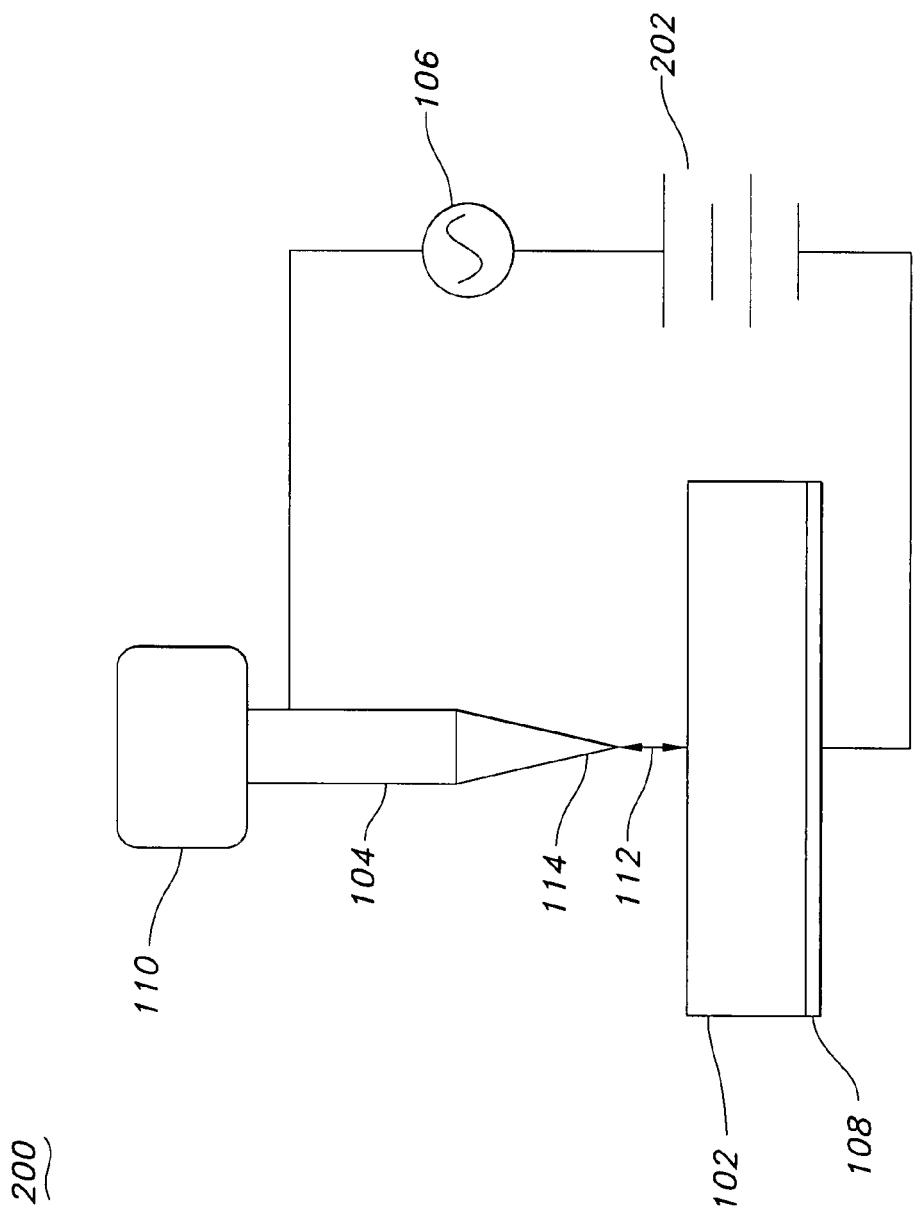
FIG. 2 is a side view illustration of an alternate exemplary apertureless THz emission microscope of the present invention.

Referring now to FIG. 2, an alternate embodiment 200 of the present invention is shown. Elements that are the same as the first exemplary embodiment are accorded the same element numbers. FIG. 2 shows a source of DC bias 202 coupled in series with the source of AC bias 106. The additional DC bias may be used to modify the surface field condition of the semiconductor sample. The source of DC bias 202 provides further optimization of the THz generation condition when combined with the source of AC bias 106. The source of DC bias 202 is desirably between about 0 to 3 V DC. The DC bias may depend upon a sample used. In other aspects this embodiment is similar to that of the first exemplary embodiment.

Figure 3:
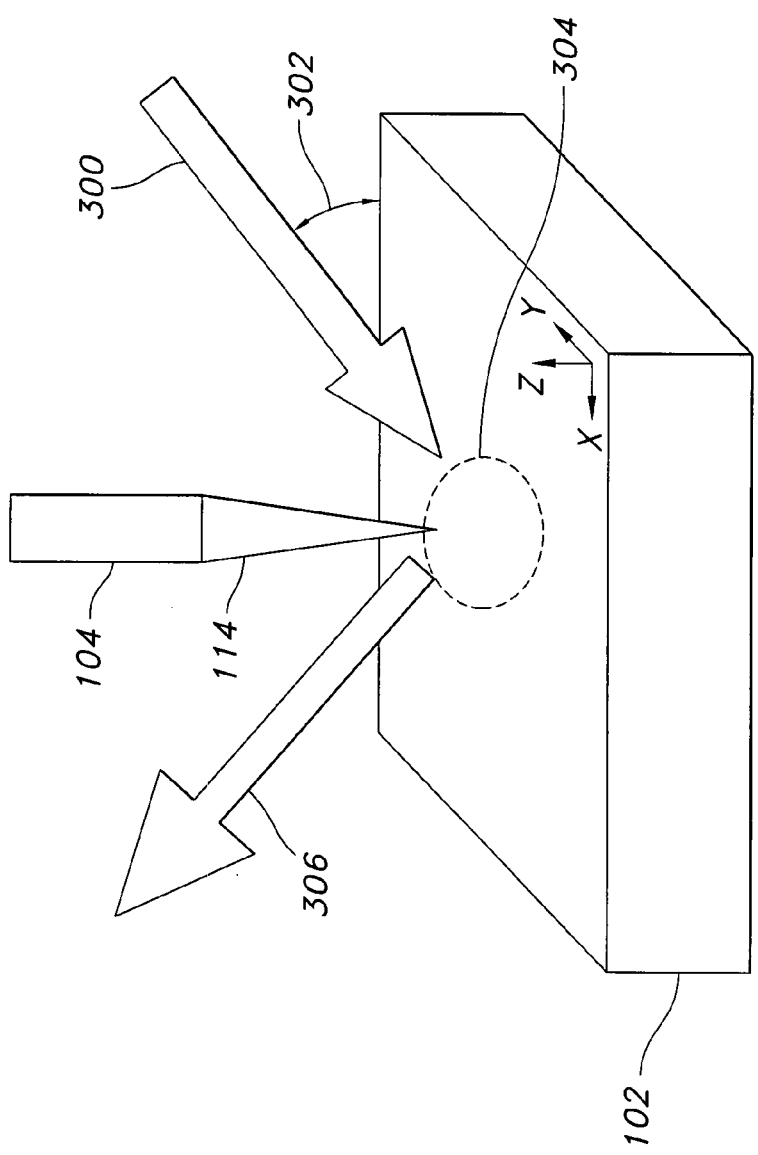
FIG. 3 is a schematic illustration of an exemplary relationship between an incident laser source and a THz emitted radiation of the present invention.

Referring now to FIG. 3, the generation of a THz emission according to active imaging is discussed. As shown in FIG. 3, an optical pump beam 300 is generated from a laser source (not shown) and impinges on the X-Y plane of substrate 102 at an incidence angle 302 near the tapered metal probe 104 forming an optical beam spot 304.

A femtosecond laser desirably generates optical beam 300 and desirably has a photon energy greater than the bandgap energy of the substrate 102. According to an exemplary embodiment of the present invention, optical beam 300 may be an 800 nm wavelength optical beam. In one exemplary embodiment, the laser source is a Ti:sapphire laser that has an average pulse generation of 100 fs, a power range of 10 to 150 mW, and a center wavelength of about 800 nm. Other femtosecond lasers providing a pulse generation width of less than or equal to 100 fs may be used, provided the frequency of the laser is above a bandwidth of the semiconductor wafer. In an exemplary embodiment, the femtosecond laser is P-polarized. The invention is not so limited, in that the laser may be S-polarized, randomly polarized or non-polarized.

Although not shown in FIG. 3, a source of AC bias 106 is applied as shown in FIG. 1 between the tapered metal probe 104 and the substrate 102. The action of the AC bias provides dipole moments below the surface of substrate 102. Optical pump beam 300 induces instant free carriers on the substrate. The AC bias converts the free carriers into a photo current and emits a THz pulse 306.

There are two mechanisms to generate THz emission according to an exemplary embodiment of the present invention. The first mechanism is the transportation of the substrate photo carrier. The second mechanism is the photo carrier acceleration in the tapered metal probe/substrate electric field. The most significant mechanism, according to the present invention, is the THz emission from the tapered metal probe/substrate electric field.

There are at least three ways to modulate the substrate surface field, each dependent upon distance 112 (shown in FIG. 1) along the Z direction between the tapered metal probe 104 and substrate 102. A distance 112 of greater than 1 nm may produce an image charge within the substrate surface, as an image of tapered metal probe 104. The image charge is driven by the AC bias and generates THz emission 306. When the metal tip 114 is within 1 nm of the substrate surface, a tunneling current between the tapered metal probe 104 and the surface of substrate surface 102 is generated. The tunneling current generates THz emission 306. When metal tip 114 is closer than 1 nm or in contact with the substrate 102, a contact current is produced and generates THz emission 306. According to an embodiment of the present invention, a smaller distance 112 and smaller tip portion 114 diameter desirably produce a higher spatial resolution.

According to an exemplary embodiment of the present invention, incidence angle 302, relative to the X-Y plane, is desirably near or at Brewster's angle. Brewster's angle is known in the art and, if used in conjunction with an P-polarized femtosecond laser, may provide a significant reduction of the reflection of the P-polarized optical beam, allowing optical power to be significantly absorbed by the substrate. Other incidence angles may be used within the scope of the present invention.

Although not shown in FIG. 3, a sample (not shown) may be placed on the surface of substrate 102 within the pump beam spot 304. THz emission is generated between the metal probe tip 114 and a sample and thus provides an image of the sample.

Figure 4:
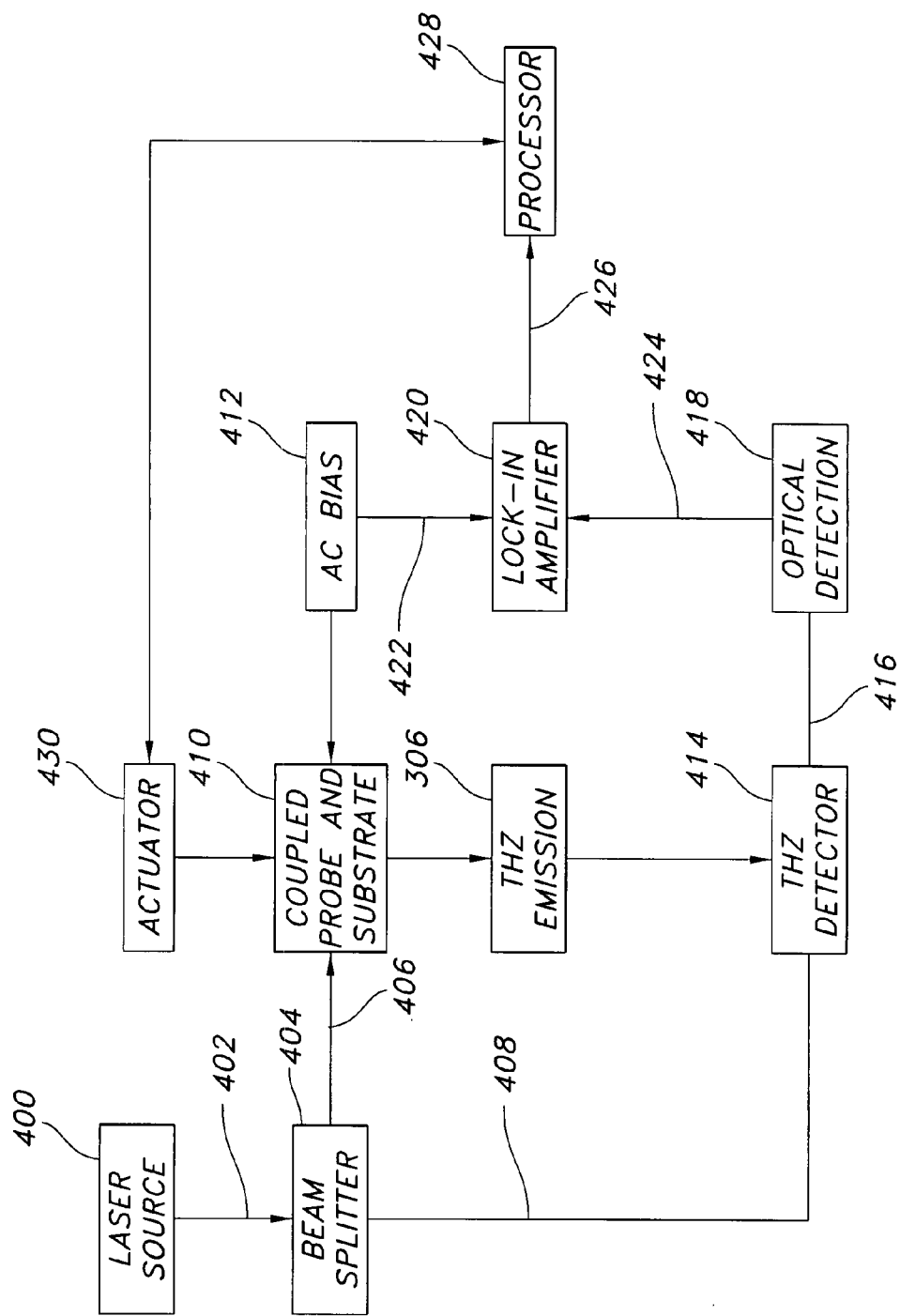
FIG. 4 is a system block diagram of an exemplary apertureless THz emission microscope system of the present invention.

FIG. 4 illustrates a system block diagram of an exemplary embodiment of the apertureless THz near-field emission microscope of the present invention. As shown in FIG. 4, a laser source 400, as described above, provides an optical beam 402 to a beam splitter 404. The beam splitter separates the optical beam 402 into beams 406 and 408 such that a portion 406 of the optical beam impinges on the tapered metal probe and substrate 410.

The tapered metal probe and substrate 410 are coupled with a source of AC bias 412. The portion 406 of optical beam 402 impinging on the AC biased coupled tapered metal probe and in turn substrate 410 generates a THz emission beam 306 (not shown in this figure).

Beam splitter 404 further provides a portion 408 of the optical beam 402 to a THz detector 414. The THz detector 414 modulates the portion 408 of the optical beam 402 with the THz emission 306. The THz detector 414 further provides the modulated portion 408 of optical beam 402 to an optical detector 418.

A lock-in amplifier 420 is provided between the source of AC bias 412 and the optical detector 418. Lock-in amplifier 420 obtains a frequency signal 422 from AC bias 412 and a resulting signal 424 from optical detection 418. Lock-in amplifier 420 filters the resulting signal 424 from optical detection 418 based on the AC frequency signal 422.

The filtered optically detected resulting signal 426 is provided to a processor 428 for processing the results to determine a THz emission image. An actuator 430 may adjust the lateral position of the tapered metal probe relative to the surface of the substrate and may provide appropriate coordinates to processor 428.

Lock-in amplifier 420 desirably acts as a narrow passband filter. The frequency of AC bias 412 is desirably used as a reference input signal 422 to provide the passband region of the filter. Lock-in amplifiers are known in the art to obtain an amplitude and phase of a signal buried in noise. Lock-in amplifier 420 may desirably reduce noise from power fluctuations in the laser source, mechanical vibrations and other external noises. Additionally, lock-in amplifier 420 may distinguish the THz emission from the substrate from the THz emission from the tip/substrate, the latter tip/substrate THz emission being the desired and dominant form of THz emission.

Processor 428 may be a portable computer or workstation computer programmed with software to provide a THz image. Processor 428 may include signal processing components such as a DSP board, A/D, D/A and other components (not shown) for collecting data from optical detector 418 and actuator 430. Although not illustrated in FIG. 4, processor 428 may also monitor other components such as laser source 400, or portions of the optical beam throughout the system. Processor 428 may be used to control the system, process image data and display captured images.

Figure 5:
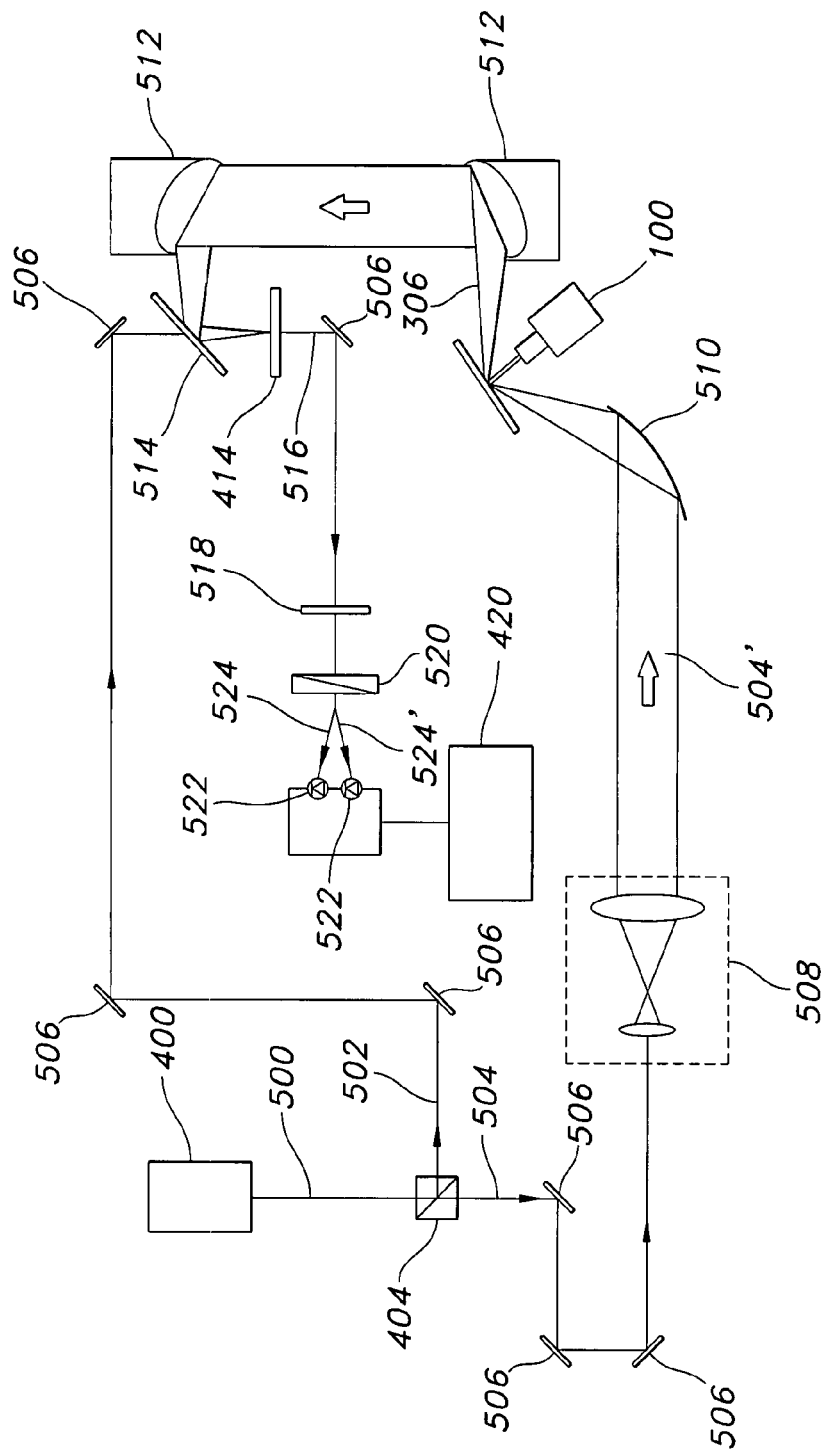
FIG. 5 is an electro-optical diagram of an exemplary apertureless THz emission microscope system of the present invention.

FIG. 5 illustrates certain electro-optical components according to an exemplary embodiment of the apertureless THz emission microscope of the present invention. Portions of this figure are described by Q. Wu and X.-C. Zhang, in "Free-space electro-optic sampling of terahertz beams," *Appl. Phys. Lett.*, 67, 3523–3525 (1995) and X.-C. Zhang et al. in patent application Ser. No. 10/434,329, incorporated herein by reference.

In the exemplary embodiment shown in FIG. 5, optical beam 500 from laser source 400 is split by beam splitter 402 into a probe beam 502 and a pump beam 504. Pump beam 504 travels through mirrors 506 which may be positioned to provide variable delay as desired. Pump beam 504 is then directed to beam expander 508.

After beam expander 508, expanded pump beam 504' is focused through parabolic mirror 510 onto exemplary apertureless THz emission microscope 100. For simplicity, the AC bias and coupling are not repeated in FIG. 5. The AC bias, coupled tip/substrate and incident pump beam onto the substrate surface causes emission of THz wave 306. A sample may be placed on the substrate surface for imaging. This THz emission may be transmitted through a sample if a sample is positioned on the substrate.

THz emitted wave 306 is then collimated and focused by parabolic mirrors 512 (which may be of similar configurations) onto a THz detector 414 by indium tin oxide (ITO) glass 514. THz detector 414 is desirably an electro-optic (EO) crystal. An exemplary EO crystal may include ZnTe, GaSe, GaP or CdTe but is not limited to these materials.

Probe beam 502 is directed to THz detector 414 by mirrors 506 and ITO glass 514. Mirrors 506 may provide variable delay of probe beam 502 as desired. ITO glass 514 desirably provides substantial reflection of the emitted THz wave 306 while allowing probe beam 502 to pass through ITO glass 514 with substantially minimal reflection.

THz detection desirably uses well-known free-space EO sampling. The field-induced birefringence of the EO crystal due to an applied electric field (THz emitted wave), modulates the polarization ellipticity of the probe beam that passes through the crystal. The ellipticity modulation of the beam can then be polarization analyzed to provide information on both the amplitude and phase of the applied electric field. The present invention analyzes a polarization change from the EO crystal and correlates it with the amplitude and phase of the THz electric field.

In THz detector 414, the electric field of the emitted THz wave 306 induces birefringence inside the EO crystal, which in turn changes the polarization of probe beam 502, by modulating it to include a component proportional to the THz wave 306. Thus, optical beam 516 leaving THz detector 414 contains information relating to THz emission 306.

Optical beam 516 is directed by mirror 506 to a well-known EO sampling system comprising a quarter waveplate 518, a Wollaston prism 520, and photo detectors 522. Quarter waveplate 518 changes the linear polarization of optical beam 516 to a circular polarization. Wollaston prism 520 splits the circular polarization of optical beam 516 into two linearly polarized beams 524 and 524', each polarized 90° relative to each other. Each polarized beam 524 and 524' is directed onto separate photo detectors 522, respectively. Photo detectors 522 may be photodiodes, for example. Photo detectors 522 are connected to circuitry (not shown), known in the art, which subtract the waveform of polarized beams 524 and 524' to eliminate the common current and thus reduce noise.

It should be noted that flat mirrors 506, beam splitter 402, and parabolic mirrors 510 and 512 are illustrated herein, as needed, to show a logical schematic diagram. More or fewer mirrors, beam splitters, and parabolic mirrors may be provided, however, as required or allowed in the physical space provided for the microscope system.

Figure 6:
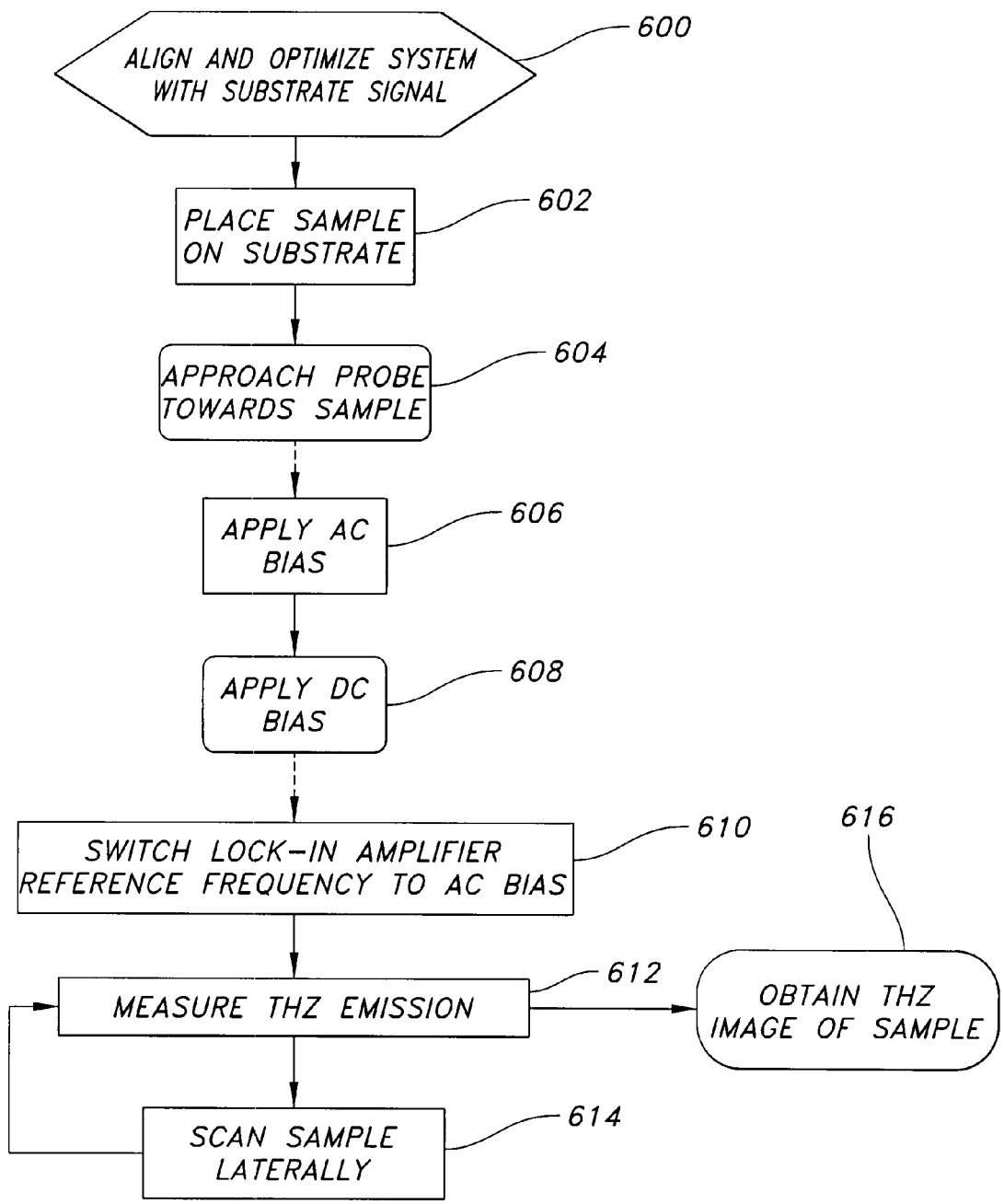
FIG. 6 is a flow chart illustrating an exemplary method of using an apertureless THz emission microscope of the present invention to generate a THz image of a sample.

FIG. 6 is a flow chart outlining a method of imaging a sample according to an exemplary embodiment of the present invention. At Step 600, the microscope system is initially aligned and optimized using a laser source with respect to a substrate signal. At Step 602, a sample may be placed on the substrate. Optionally, at Step 604, the tapered metal probe may be positioned toward the sample if the tapered metal probe is not already in contact with the sample.

At Step 606, an AC bias voltage is desirably applied between the tapered metal probe and substrate. At Step 608, a DC bias voltage may additionally be applied to further optimize the conditions for generating THz emission according to alternate embodiment 200 of FIG. 2. It should be noted that the order of Steps 606 and 608 may be reversed or combined into a single step.

At Step 610, a lock-in amplifier is turned on and the frequency of the AC bias is provided to the lock-in amplifier as a reference signal for bandpass filtering.

At Step 612, THz emission from the tapered metal probe/substrate is measured using the THz detector and optical detection system as described above. At Step 614, the probe is desirably repositioned laterally with respect to the sample and at Step 612, the THz emission is again measured. The process of repositioning the tapered metal probe of Step 614, and measuring THz emission of Step 612, is continued until a THz image of the sample is obtained, at Step 616.

The invention will next be illustrated by reference to a number of examples. The examples are included to more clearly demonstrate the overall nature of the invention. These examples are exemplary, not restrictive of the invention.

EXAMPLE 1

FIGS. 7a–d compare THz signals emitted from a semiconductor wafer to THz signals emitted in the presence of the tapered metal probe in the time-domain for n-type and p-type GaAs and InAs semiconductors. The signals emitted from the semiconductor wafer are measured without a bias voltage applied to the wafer. The wafer signal is generated from the wafer surface itself according to known in the art methods. The THz signals emitted in the presence of the tapered metal probe are measured according to the method and system described above when the tapered metal probe is at least in contact or less than 10 nm from the wafer surface.

A variety of semiconductor wafers were tested. One material was InAs of a) n-type doped with a concentration of about $3 \times 10^{16}$ and $1 \times 10^{17}$ cm$^{-3}$ and b) p-type doped with a concentration of about $2 \times 10^{17}$ and $2 \times 10^{18}$ cm$^{-3}$. A second material was GaAs of a) n-type doped with a concentration of between $1 \sim 5 \times 10^{17}$ and about $2 \times 10^{18}$ cm$^{-3}$ and b) p-type doped with a concentration of between $1 \sim 5 \times 10^{17}$ and about $2 \times 10^{18}$ cm$^{-3}$.

Figure 7A:
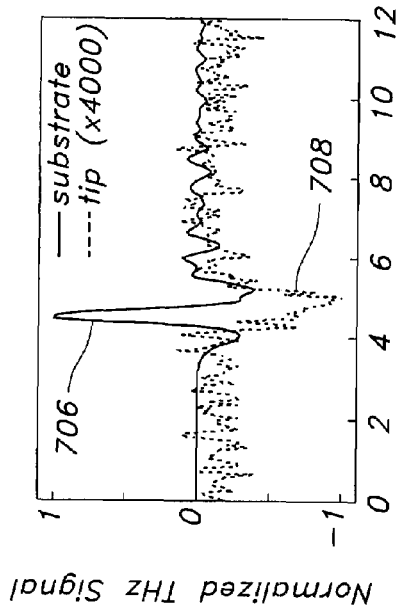
FIGS. 7a–7d are time-domain graphs comparing normalized THz emission from a bare wafer (wafer signal) and from a wafer/metal probe modulated by AC bias (tip signal) according to semiconductor material and dopant.
Figure 7B:
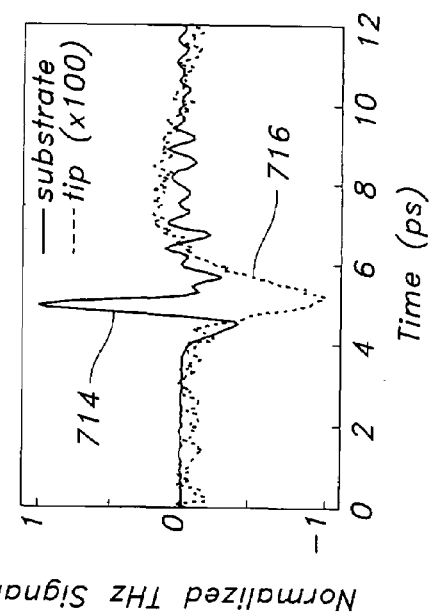
Figure 7C:
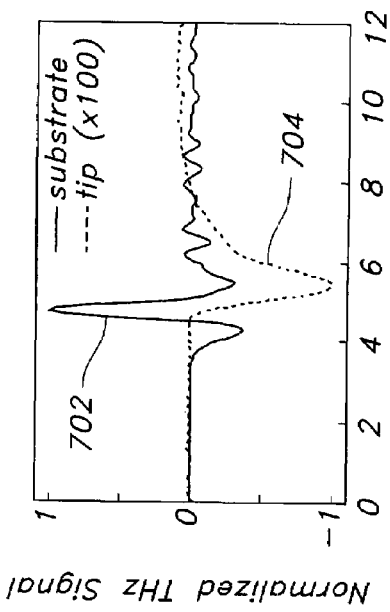
Figure 7D:
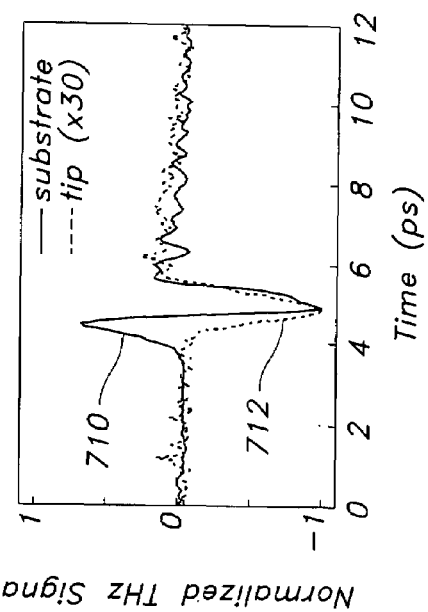

All THz signals with the tapered metal probe in place are normalized to provide a feature comparison of the wafer and probe THz emitted signals. FIG. 7a compares p-type InAs of $1 \times 10^{16}$ cm$^{-3}$ concentration for the wafer 702 and probe 704. The probe signal was normalized by a multiplication factor of 100. FIG. 7b compares n-type InAs of $3 \times 10^{16}$ cm$^{-3}$ concentration for the wafer 706 and probe 708. The probe signal was normalized by a multiplication factor of 4000. FIG. 7c compares p-type GaAs of $1 \sim 5 \times 10^{17}$ cm$^{-3}$ concentration for the wafer 710 and probe 712. The probe signal was normalized by a multiplication factor of 30. FIG. 7d compares n-type GaAs of $1 \sim 5 \times 10^{17}$ cm$^{-3}$ concentration for the wafer 714 and probe 716. The probe signal was normalized by a multiplication factor of 100.

Depending on the dopant types and densities, the THz signals from the probe were reduced by factors of 100~1000 compared with those from the bare wafers. In the samples tested, larger probe signals were observed from p-type semiconductors. The wafer signals from p-type and n-type InAs had the same polarity, while the wafer signals from p-type and n-type GaAs had opposite polarities. However, regardless of the dopant types, the probe signals had the same polarity for both InAs and GaAs in contrast to the substrate signals.

EXAMPLE 2

Figure 8:
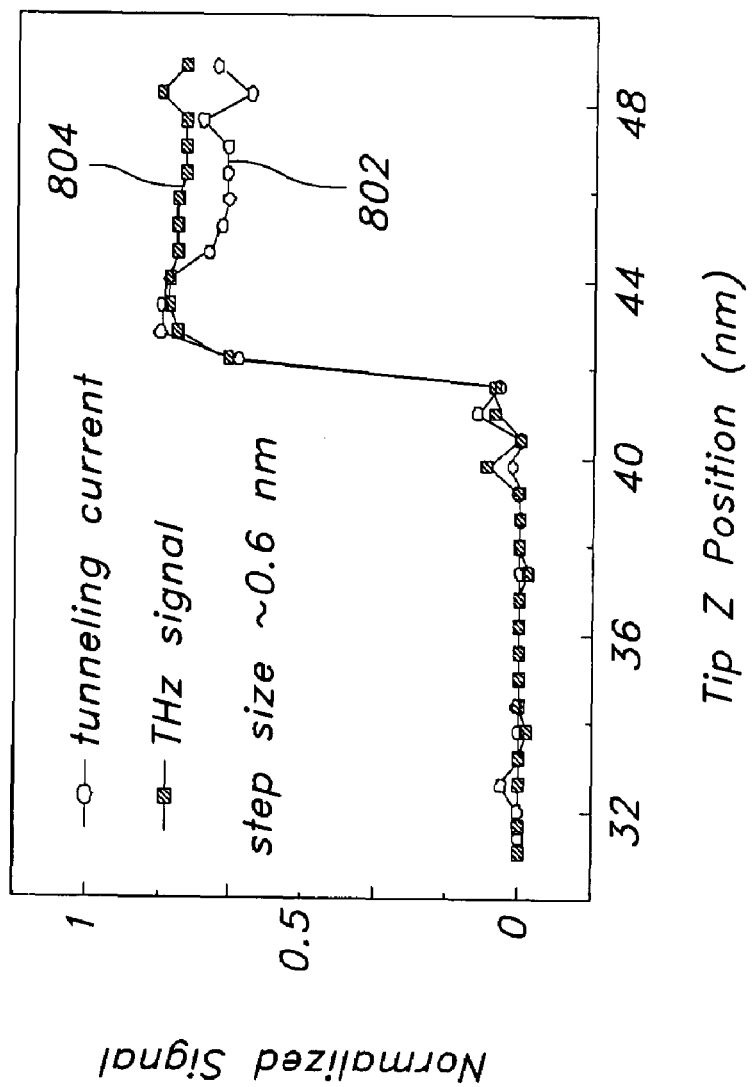
FIG. 8 is a normalized graph comparing an instantaneous measurement of tunneling current and THz emitted signal as a metal probe vertically approaches a semiconductor substrate.

FIG. 8 compares the THz emitted signal from the tapered metal probe/substrate and the current of the probe, measured simultaneously, as the tapered metal probe approached the substrate surface. For the experiment, a p-type, $1 \times 10^{16}$ cm$^{-3}$ InAs semiconductor wafer was used as the substrate. The probe was driven by a piezo actuator with a step size of approximately 0.6 nm.

The results of FIG. 8 show that the onsets of a tunneling current 802 and THz emission signal 804 appeared almost exactly at the same tapered metal probe location. This indicates that the tunneling current and the THz signal are closely correlated to each other. The 10% to 90% transition in the tapered metal probe signal occurred within 1 nm, demonstrating a nanometer resolution in the vertical direction.

EXAMPLE 3

Figure 9A:
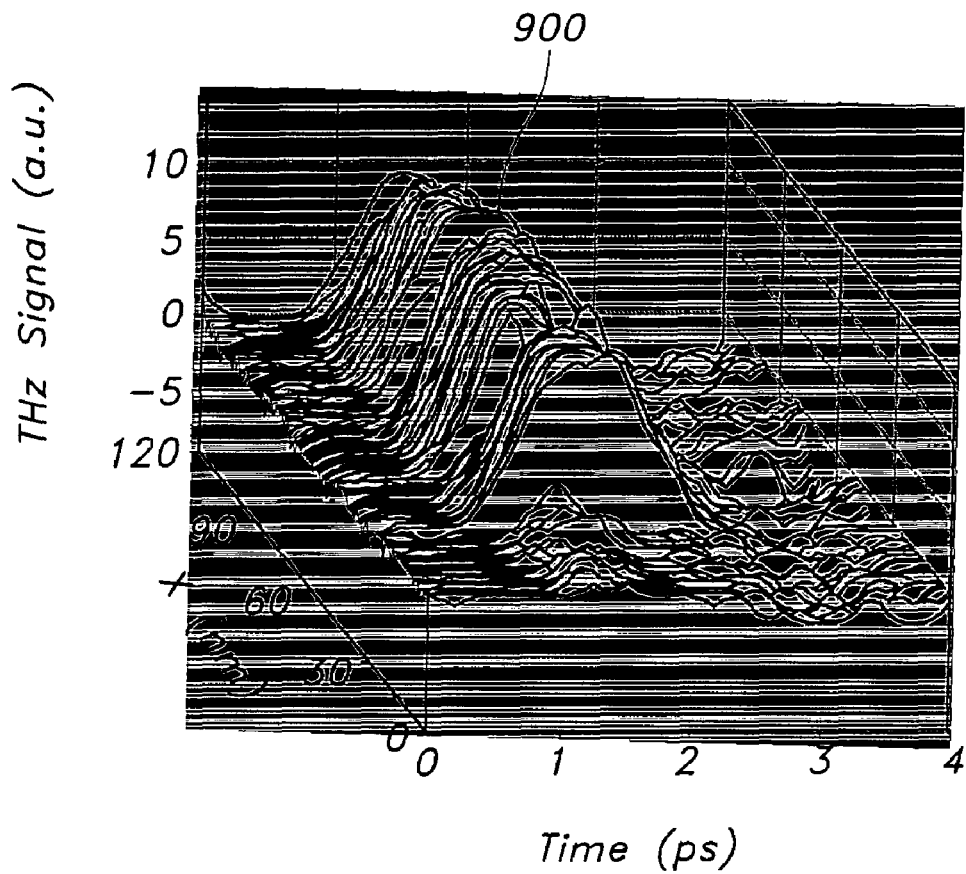
FIG. 9a is a THz image after scanning an edge of a metal film sample.

FIG. 9a shows a THz image 900 when the metal probe is scanned across the edge of a Cr/Au film deposited on a p-type InAs substrate. The average thickness of the metal film was 25 nm, and the tip diameter was 40 nm. The scanning range was approximately 5 µm with a step size of 1 nm. Measurement with an atomic force microscope showed that near the edge, the thickness of the metal film gradually changed to 0 over a 100 nm range.

Figure 9B:
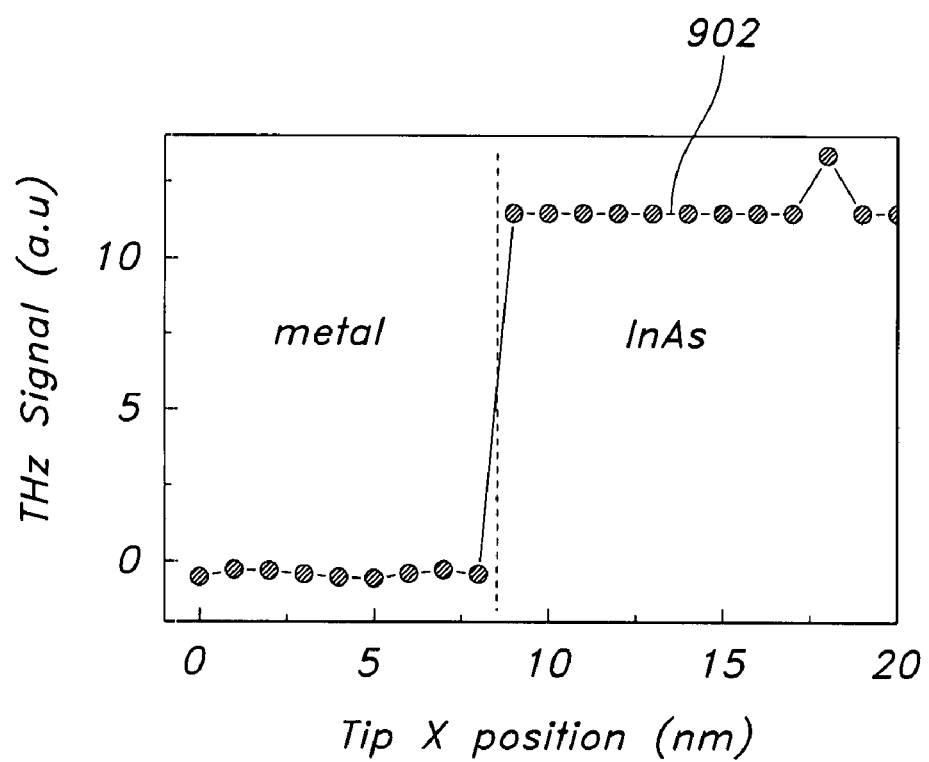
FIG. 9b is a peak amplitude of the THz image compared to probe position after scanning the edge of the Cr/Au film sample.

FIG. 9b shows the peak amplitude 902 of THz image 900 with probe position. It was found that the THz signal changed abruptly within 1 nm in temporal shape and polarity when the tip was scanned from the metal to InAs surfaces. Although not shown, the procedure was repeated with a InAlAs/InP interface where a 1 µm thick InAlAs was grown on a semi-insulating InP substrate. At the InAlAs/InP heterojunction, a transition of the probe signal within 2.5 nm was observed. It is expected that the lateral resolution may be improved if the tip diameter is reduced.

EXAMPLE 4

Figure 10:
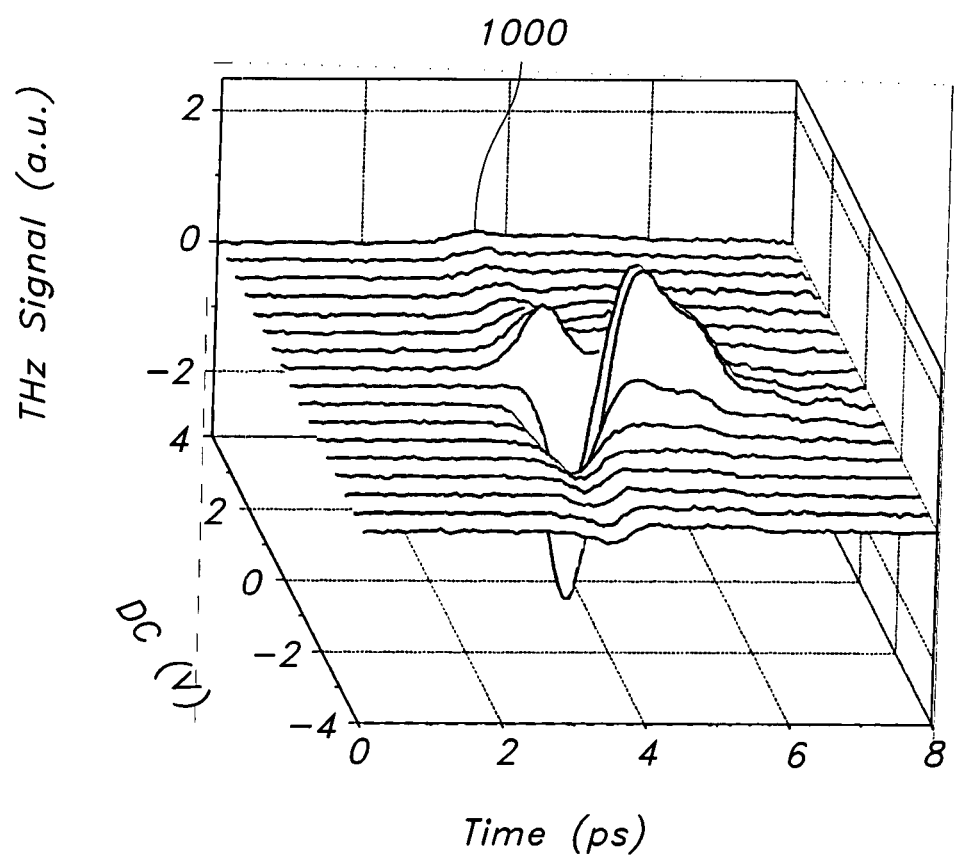
FIG. 10 is a graph of a THz probe signal with fixed AC bias and variable DC bias.

FIG. 10 shows the relationship between a fixed AC bias and a variable DC bias on a THz probe signal. When a combination of both AC and DC bias voltages are applied to the probe/substrate, a nonlinear relationship between an electric field and the bias may change a temporal shape and a frequency spectrum of the probe signal. A probe signal 1000 in the time domain is measured from a substrate of p-type InAs. The AC bias was fixed at 1 V (peak to peak for a square wave). The DC bias was varied between –4 to 4 V.

A positive voltage on the probe/substrate interface provided a reverse bias. THz probe signal 1000 showed waveform distortion and reshaping at different DC bias voltages, due to the bias scanning through a forward bias, reverse bias and breakdown regimes. The nonlinear change of the waveform may be provided by a field-dependent transient photocurrent at the probe/substrate interface. Adjusting the amplitude of AC bias and DC bias shows that an optimal probe signal may be obtained when the AC bias fully switches the probe/substrate interface field and a DC bias is also applied. The results imply that transient photocarriers within the modulated field on the substrate surface under the probe are the source of the THz probe signal. By taking advantage of a spectral sensitivity to the DC bias, the method of the present invention may provide further information regarding transient carrier dynamics and electric field distribution in nano-scale devices.

EXAMPLE 5

Figure 11:
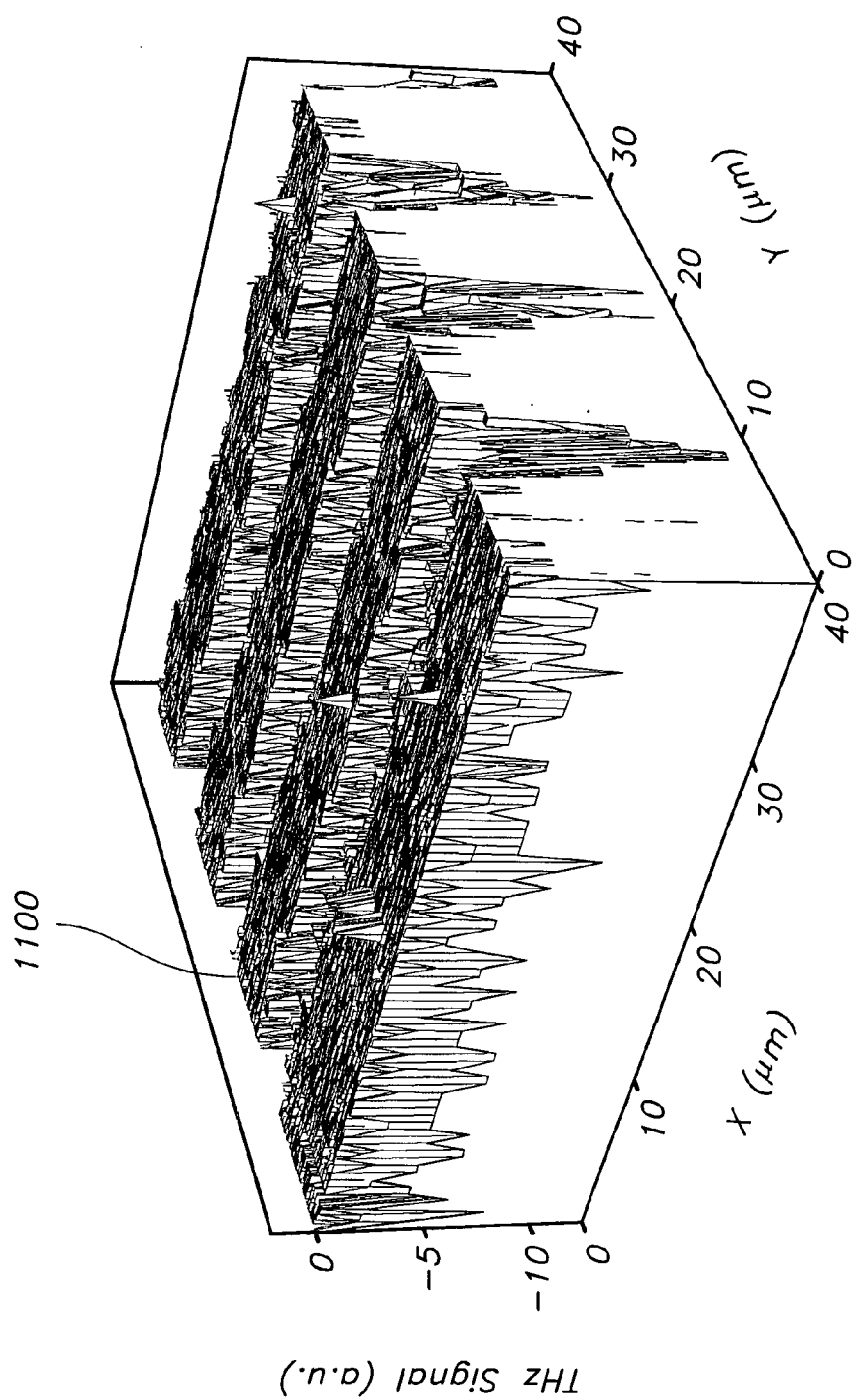
FIG. 11 is a THz image after scanning a metal grating structure.

FIG. 11 shows a THz image 1100 when the metal probe is scanned across a Cr/Au grating structure deposited on a p-type InAs substrate. A period of the grating is 10 µm with a metallic line width equal to 6 µm. The scanning of the tip was performed using a feedback control with a constant contact current mode to maintain tip contact with the grating during the scan. The scanning step size was 100 nm across the grating and 500 nm along the grating.

The present invention provides advantages in resolution capability. The inventors have determined that the resolution by this method is less than 0.1 nm and 1 nm in vertical and lateral directions, respectively. The demonstrated later resolution is much smaller than the size of the probe. Even if the probe diameter is 40 nm, THz wave emission from an InAs substrate shows a lateral resolution of 1 nm, which is approximately $1/1,000,000$ of a central wavelength of an emitted THz signal. The transition range is within a few lattice constants of the substrate. Further, the coupled dipole interaction between the probe and sample surface may be tailored by tuning the wavelength of the pump laser and selectively exciting dipole moments below the sample surface. Additionally, if the excited dipole moments are localized in nanostructures such as quantum dots and wires, the spatial resolution may be significantly enhanced.

The AC bias of the present invention provides a reference signal for measuring the THz emission from the tapered metal probe and substrate interface. When the optical pump beam chopping frequency is used as a reference signal to the lock-in amplifier, the wafer signal may be measured. When the AC bias is used as the reference signal to the lock-in amplifier, however, only the metal probe signal is measured, even though the wafer signal has a higher amplitude than the metal probe signal. The metal probe signal may thus be recorded because it is modified at the reference frequency of the AC bias.

The present invention provides a simplified system compared to prior art THz microscopes and allows use of a conventional laser source to generate THz emission. A conventional laser source is easier to manipulate and the optics in the optical regime are well-developed.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A device for use with a source of radiation to provide a THz emission image representing a sample, the device comprising:
   a substrate;
   a metallic based probe disposed adjacent a first surface of the substrate, the probe having a tip portion at one end thereof; and
   a source of AC bias coupled between the metallic based probe tip and a further surface of the substrate,
   wherein radiation generated by the source of radiation is incident upon the first surface of the substrate in a vicinity of the metallic based probe tip, and a THz radiation is emitted from the first surface of the substrate based at least on the AC bias.

2. The device according to claim 1, the device further comprising:
   a THz detector;
   means for impinging and focusing a) a portion of the radiation from the source of radiation and b) at least a portion of the THz radiation emitted from the substrate onto a surface of the THz detector, the THz detector modulating the portion of the radiation from the source of radiation with the THz radiation to create a modulated THz radiation; and
   means of optical detection for detecting the modulated THz radiation.

3. The device according to claim 2, further comprising a lock-in amplifier coupled to the means of optical detection and the source of AC bias, a frequency of the AC bias provided to the lock-in amplifier.

4. The device according to claim 3, wherein the lock-in amplifier reduces a noise level due to at least one of power fluctuations of the source of radiation, mechanical vibrations and background THz radiation noise based on the frequency of the AC bias.

5. The device according to claim 3, wherein the lock-in amplifier comprises a bandpass filter to filter the modulated THz radiation based on the frequency of the AC bias.

6. The device according to claim 1, wherein the source of radiation is a femtosecond laser.

7. The device according to claim 6, wherein the femtosecond laser is one of a p-polarized, an s-polarized, a randomly polarized or a non-polarized laser.

8. The device according to claim 1, further comprising an actuator coupled to the metallic based probe for changing at least one of a) a distance between the tip of the metallic based probe and the first surface of the substrate and b) a placement of the tip of the metallic based probe within a plane parallel to the first surface of the substrate.

9. The device according to claim 1, further comprising a source of DC bias coupled in series with the source of AC bias.

10. The device according to claim 9, wherein the source of DC bias generates a voltage between about −3 V to 3 V DC.

11. The device according to claim 1, wherein the source of AC bias generates a voltage between about 0 V to 5 V rms.

12. The device according to claim 1, wherein the substrate comprises a semiconductor wafer of at least one of a p-type and/or an n-type semiconductor material.

13. The device according to claim 12, wherein the semiconductor wafer comprises at least one of GaAs and/or InAs.

14. The device according to claim 1, wherein the metallic based probe comprises at least one of Tungsten and/or Pt—Ir.

15. The device according to claim 1, wherein the tip portion of the metallic based probe comprises a diameter of between about 1 nm to 1 µm.

16. The device according to claim 1, wherein the first surface of the substrate is adapted to receive the sample for imaging.

17. A method for providing a THz emission image representing a sample, for use with a source of radiation, the method comprising the steps:
providing a substrate;
disposing a metallic based probe adjacent a first surface of the substrate, the metallic based probe having a tip portion at one end thereof;
providing a source of AC bias coupled between the metallic based probe and a further surface of the substrate;
emitting the radiation from the source of radiation toward the first surface of the substrate in a vicinity of the tip portion of the metallic based probe; and
emitting a THz radiation from the first surface of the substrate responsive to at least the AC bias based on the radiation emitted from the source of radiation.

18. The method according to claim 17, the method further comprising:
providing a THz detector;
impinging and focusing a) a portion of the radiation from the source of radiation and b) at least a portion of the emitted THz radiation emitted from the substrate onto a surface of the THz detector, the THz detector modulating the source of radiation with the THz radiation to provide a modulated THz radiation; and
optically detecting the modulated THz radiation.

19. The method according to claim 18, further comprising the step of bandpass filtering the optically detected modulated source of radiation based on an AC bias frequency provided by the source of AC bias.

20. A microscope for use with a source of radiation for producing a THz emission representing an image of a sample, the microscope comprising:
a substrate;
a metallic based probe disposed adjacent a first surface of the substrate, the probe having a tip portion at one end thereof;
a source of AC bias coupled between the metallic based probe tip and a further surface of the substrate;
an actuator coupled to the metallic based probe, the actuator changing an X and/or Y axis position of the metallic based probe relative to a plane parallel to the first surface of the substrate;
a THz detector for modulating the source of radiation with a sample-modified THz radiation to create a modulated THz radiation characteristic of the sample;
an optical detection system for modifying and detecting the modulated THz radiation and converting the modulated THz radiation into electronic information; and
a processor for receiving the electronic information and producing an image of the sample based on the electronic information and the position provided from the actuator,
wherein the sample is placed on the substrate, and radiation generated by the source of radiation is incident upon the first surface of the substrate in a vicinity of the metallic based probe tip and sample, and the sample-modified THz radiation is emitted from the first surface of the substrate based at least on the AC bias.

21. The microscope according to claim 20, further comprising a lock-in amplifier coupled to the optical detection system and a frequency of the AC bias provided to the lock-in amplifier, the lock-in amplifier bandpass filtering the modulated THz radiation at the frequency of the AC bias.

22. The microscope according to claim 20, wherein the actuator further changes a Z axis distance between the metallic based probe tip and the first surface of the substrate.

23. The microscope according to claim 22, wherein the distance is greater than 1 nm for providing an image charge that emits the THz radiation.

24. The microscope according to claim 22, wherein the distance is less than 1 nm for providing a tunneling current that emits the THz radiation.

25. The microscope according to claim 22, wherein the metallic based probe tip is at or significantly close to the first surface of the substrate for providing a contact current that emits the THz radiation.

* * * * *